US012618986B2

(12) United States Patent
Grasruck et al.

(10) Patent No.: US 12,618,986 B2
(45) Date of Patent: May 5, 2026

(54) DETECTOR MODULE FOR AN X-RAY DETECTOR

(71) Applicants: Michael Grasruck, Eckental Forth (DE); Stefan Wirth, Erlangen (DE); Hannes Monius, Forchheim (DE); Gottfried Tschöpa, Baiersdorf (DE); Stefan Wölfel, Dormitz (DE); Michael Teuber, Forchheim (DE)

(72) Inventors: Michael Grasruck, Eckental Forth (DE); Stefan Wirth, Erlangen (DE); Hannes Monius, Forchheim (DE); Gottfried Tschöpa, Baiersdorf (DE); Stefan Wölfel, Dormitz (DE); Michael Teuber, Forchheim (DE)

(73) Assignee: Siemens Healthineers AG, Forchheim (DE)

( * ) Notice: Subject to any disclaimer, the term of this patent is extended or adjusted under 35 U.S.C. 154(b) by 166 days.

(21) Appl. No.: 18/427,801

(22) Filed: Jan. 30, 2024

(65) Prior Publication Data

US 2024/0255657 A1     Aug. 1, 2024

(30) Foreign Application Priority Data

Jan. 31, 2023    (DE) ..................... 10 2023 200 767.3

(51) Int. Cl.
| | |
|---|---|
| *G01T 1/20* | (2006.01) |
| *A61B 6/42* | (2024.01) |
| *G01N 23/046* | (2018.01) |
| *G01N 23/083* | (2018.01) |
| *G01T 1/24* | (2006.01) |

(52) U.S. Cl.
CPC .......... *G01T 1/2002* (2013.01); *A61B 6/4291* (2013.01); *G01N 23/046* (2013.01); *G01N 23/083* (2013.01); *G01T 1/20182* (2020.05); *G01T 1/20188* (2020.05); *G01T 1/243* (2013.01)

(58) Field of Classification Search
CPC .................................................... A61B 6/4291
See application file for complete search history.

(56) References Cited

U.S. PATENT DOCUMENTS

| | | | |
|---|---|---|---|
| 7,235,788 B2 | 6/2007 | Von | |
| 2002/0064252 A1* | 5/2002 | Igarashi ................... | A61B 6/06 |
| | | | 378/19 |
| 2005/0109946 A1 | 5/2005 | Von | |
| 2006/0054832 A1 | 3/2006 | Cambensi | |
| 2007/0064878 A1 | 3/2007 | Heismann | |
| 2017/0269236 A1* | 9/2017 | Wirth ................... | A61B 6/4233 |
| 2018/0064407 A1* | 3/2018 | Beacham ............. | G01T 1/2002 |

(Continued)

FOREIGN PATENT DOCUMENTS

| | | |
|---|---|---|
| DE | 10354497 A1 | 6/2005 |
| DE | 102004044901 A1 | 3/2006 |
| DE | 102005044650 A1 | 3/2007 |

*Primary Examiner* — Casey Bryant
(74) *Attorney, Agent, or Firm* — Lempia Summerfield Katz LLC

(57) ABSTRACT

A detector module for an X-ray detector includes at least one sensor unit for detecting X-rays, and at least one anti-scatter grid in a stacking arrangement with the at least one sensor unit. The at least one sensor unit is fixed in place on the at least one anti-scatter grid. The at least one anti-scatter grid includes a fastener for securely mounting the detector module on a carrier unit of the X-ray detector.

19 Claims, 4 Drawing Sheets

(56) References Cited

U.S. PATENT DOCUMENTS

| 2019/0072679 | A1* | 3/2019 | Ye | ......................... | A61B 6/4291 |
| 2019/0282185 | A1* | 9/2019 | Gregerson | ........... | A61B 6/4488 |
| 2021/0298698 | A1* | 9/2021 | Yu | ............................ | A61B 6/06 |

* cited by examiner

DETECTOR MODULE FOR AN X-RAY DETECTOR

This application claims the benefit of German Patent Application No. DE 10 2023 200 767.3, filed on Jan. 31, 2023, which is hereby incorporated by reference in its entirety.

BACKGROUND

The present embodiments relate to a detector module for an X-ray detector, to an X-ray detector, and to a computed tomography device including such an X-ray detector.

Independent of the grammatical term usage, individuals with male, female or other gender identities are included within the term.

X-ray detectors are often used for medical imaging examinations of patients. In a computed tomography device (CT device), for example, the X-ray detector and the X-ray source are mounted diametrically opposite each other on a rotor. During the scanning of an object that is to be imaged, the object is positioned in an examination region of the CT device, and the X-ray source and the X-ray detector rotate around the object while the X-ray source emits X-rays. The X-rays traversing the object are detected by one or more detector elements, also referred to as detector pixels or pixel elements, of the X-ray detector, and a measurement signal is generated based on the locally captured X-rays. Because the X-rays interact according to local properties of the object when passing through the object, and, for example, are attenuated, it is possible in this way to make inferences about properties of the object.

In order to suppress the scattered radiation resulting during a scan and potentially leading to a reduction in image quality, X-ray detectors are equipped with anti-scatter collimators, referred to in the following as anti-scatter grids (ASGs). In this case, current-generation CT devices are often equipped with what are referred to as three-dimensional (3D) anti-scatter grids that have an essentially three-dimensional grid structure. These 3D anti-scatter grids enable the scattered radiation to be suppressed in the radial (e.g., φ direction, direction of rotation) and in the axial direction (e.g., feedforward direction, perpendicular to the direction of rotation). Further, in addition to such three-dimensional grid structures, in simpler implementations of anti-scatter grids, it is also possible to use grids of a type that provide collimator walls along one direction only and consequently suppress scattered radiation along the one direction.

An X-ray detector for a CT device typically consists of individual modules that are fixed in place in a carrier unit of the X-ray detector. In this case, the individual module consists of at least one anti-scatter grid and a sensor unit for detecting X-rays. Typically, these functional units are mounted on a carrier (e.g., module carrier) that is included in the detector module and in turn includes means for fixing the module in place in the X-ray detector.

First, it is known in this case to join the anti-scatter grid to the sensor unit by adhesive bonding and to fix the unit in place on the module carrier, which is in turn configured to be securely mounted in the X-ray detector. Second, structures are also known in which both the sensor unit and the anti-scatter grid are connected separately to a module carrier. In this case, the anti-scatter grid then spans the sensor unit in the manner of a bridge.

For example, but not just in the case of a CT device, for achieving optimal image quality, the imaging components are to be aligned and mounted very precisely relative to one another. This consequently applies also to the arrangement of an anti-scatter grid relative to the sensor unit of the X-ray detector or the arrangement of the anti-scatter grid in the X-ray detector itself.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved detector module for an X-ray detector that reduces tolerances occurring between an anti-scatter grid and a sensor unit or a position of the module in the X-ray detector is provided. As another example, an improved X-ray detector and an improved computed tomography device are provided.

The present embodiments relate to a detector module for an X-ray detector including at least one sensor unit for detecting X-rays and at least one anti-scatter grid disposed in a stacking arrangement with the sensor unit. The sensor unit is fixed in place on the anti-scatter grid, and the anti-scatter grid has fastening means (e.g., fasteners) for securely mounting the detector module on a carrier unit of the X-ray detector.

The sensor unit may include a converter unit that is configured to convert incident X-rays into an electrical signal, and a readout unit that is configured to process the electrical signals from the converter unit.

The converter unit may in this case include a direct-converting or an indirect-converting converter material. In direct-converting sensor units, the X-rays or the X-ray photons may be converted into electrical signals by a suitable converter material. Examples for use as converter material include CdTe, CZT, CdZnTeSe, CdTeSe, CdMnTe, InP, TlBr2, HgI2, GaAs, and so forth. In indirect-converting sensor units, the X-rays or the photons may be converted into light by a suitable converter material and into electrical pulses by optically coupled photodiodes (e.g., a photodiode array). Scintillators (e.g., GOS (Gd2O2S), CsJ, YGO or LuTAG) may be employed as the converter material in this case. The converter unit may, for example, have a planar dimension along two directions extending perpendicularly to the stacking direction of the stacking arrangement. The converter unit may be embodied as one piece in a unitary construction or be composed of a plurality of converter elements positioned adjacent to one another along the planar dimension.

A readout unit generally serves for digitizing the electrical signals that are fed in by the converter unit. However, the readout unit may also make provision for more extensive processing operations. A readout unit may be implemented, for example, as an application-specific integrated circuit (ASIC). It is also possible for multiple readout units to be assigned to a unitary or composite sensor unit.

In both types, indirect-converting or direct-converting, the sensor unit may include a plurality of pixel elements (e.g., the smallest planar areas that may be read out independently). In order to be read out, each pixel is connected to an associated evaluation pixel element of a readout unit.

In embodiments, the converter unit is implemented as an indirect-converting converter unit. This may facilitate a fixing of the anti-scatter grid in place directly on the converter unit since the converter material used is often mechanically more robust and less susceptible.

According to the present embodiments, the anti-scatter grid is present in the form of a stacking arrangement with the sensor unit. The stacking direction of the stacking arrangement extends substantially parallel to a radiation incidence direction of X-rays for exposing an X-ray detector when the detector module is used in such a detector.

The anti-scatter grid includes a plurality of collimator walls that are arranged adjacent to one another in at least a first direction perpendicular to a stacking direction. The first direction may then extend, for example, substantially perpendicularly to the radiation incidence direction. The collimator walls are configured or aligned substantially parallel to the stacking direction and are arranged adjacent to one another along the first direction. A deviation of the parallel alignment from the stacking direction of up to 10 degrees (e.g., of less than 5 degrees) may be included. This may include that the collimator walls may be aligned slightly inclined onto a focal point of an X-ray source arranged for the purpose of exposing an X-ray detector by which the anti-scatter grid is encompassed. In this case, the collimator walls are arranged spaced apart relative to one another, such that a thoroughfare channel is provided in each case between two adjacent collimator walls. The alignment substantially along the stacking direction permits the passage of the X-rays from the radiation incidence direction through the anti-scatter grid, whereas X-rays scattered from the radiation incidence direction, which may have a negative impact on the image quality, may be absorbed by the collimator walls.

In addition to the above-described first plurality of collimator walls, the anti-scatter grid may also have a second plurality of collimator walls that are arranged adjacent to one another in a second direction perpendicular to the first direction and perpendicular to the stacking direction. As a result, a 3D anti-scatter grid including a grid-shaped collimator module that enables an improved suppression of the scattered radiation along two directions and thus allows an improvement in image quality to be achieved is provided.

The collimator walls may include a material that absorbs X-rays such that a suppression of scattered radiation that occurs when an object is exposed and irradiated in an imaging application is provided to a sufficient extent, at least along the first direction. The collimator walls include, for example, a material that strongly absorbs X-rays (e.g., has a high absorption coefficient for X-rays; a higher absorption coefficient than bone tissue). For example, the collimator walls may include a metallic material. The collimator walls may include tungsten. However, the plurality of collimator walls may also include lead, molybdenum, zinc, or another material or a composite material.

The fixing of the sensor unit in place on the anti-scatter grid is configured, such way that the connection withstands the forces being exerted during an imaging application. Before the sensor unit is fixed in place, the anti-scatter grid is aligned relative to the sensor unit (e.g., to the pixel elements).

A fixing of the sensor unit in place on the anti-scatter grid may be achieved by an adhesive bonding of the sensor unit to the anti-scatter grid. A permanent connection may be created. In this case, use may be made of an adhesive that does not impede the detection of X-rays in such a way as to have an adverse effect on image quality. The adhesive may include a material having a lower absorption coefficient than the material of the collimator walls. In embodiments, the layer of adhesive for gluing the sensor unit to the anti-scatter grid absorbs less than 5 percent or less than 3%, of a radiant energy that is effective for the imaging. The amount of radiant energy effective for the imaging may denote the radiant energy that would impinge on the detection surface of the detector element, for example, after passing through the anti-scatter grid without adhesive bonding or that would be detected by the detector element. The adhesive may be based, for example, on an epoxy resin, an acrylic resin, or some other potting compound or bonding material.

For example, an adhesive bonding with a scintillator may also be implemented using a reflector adhesive. However, a non-reflecting adhesive may also be used.

The fastening means, which are embodied on the anti-scatter grid, serve for securely mounting the detector module including the stacking arrangement composed of sensor unit and anti-scatter grid to a carrier unit of the X-ray detector. The fastening means may be implemented in different ways provided the fastening means are suitable for achieving a stable mounting of the detector module in the X-ray detector that is also present unchanged when acted upon by the forces exerted during an imaging application (e.g., the centrifugal forces acting on the module during a CT imaging session). In this case, the fastening means may cooperatively interact with corresponding (counter-)fastening means (e.g., counter-fasteners) on the carrier unit of the X-ray detector. The fastening means may be configured, for example, as drilled holes, recesses, or pins. Drilled holes may be configured, for example, such that the drilled holes are suitable for a screw-type connection between carrier unit and detector module. Different fastening means may be embodied on an anti-scatter grid; for example, a drilled hole for a screw-type connection may be embodied on one side of the anti-scatter grid, and a pin may be provided on the other side.

The carrier unit may be configured such that a plurality of detector modules may be fixed in place thereon. The carrier unit may form a frame (e.g., a carrier frame) within which the detector module or detector modules may be arranged and secured. The carrier unit may be, for example, a part of the housing of the X-ray detector.

Since it may be achieved by the fastening means, which are embodied on the anti-scatter grid and serve to secure the module in the X-ray detector, that, in contrast to mounting the detector module including the stacking arrangement composed of sensor unit and anti-scatter grid on a module carrier, via which the mounting in the X-ray detector is achieved, the tolerance resulting when the sensor unit is mounted relative to the carrier is eliminated. This enables the sensor unit to be inserted more accurately in the carrier unit (e.g., in the X-ray detector). Further, compared to a separate mounting of the sensor unit and an anti-scatter grid on a module carrier, the tolerance chain in the case of the relative arrangement via the module carrier is also removed. Further, a cost-effective component may be achieved by dispensing with the module carrier.

In embodiments, the anti-scatter grid may include, for example, a collimator module including the plurality of collimator walls and, on each of two opposite external sides of the collimator module, a retaining element on which the fastening means are embodied. In this case, the external sides are, for example, those sides of the collimator module having planar dimensions that extend parallel to the stacking direction of the stacking arrangement. The retaining elements may be embodied, for example, on those sides on which no sequential arrangement of detector modules is provided in an X-ray detector. When the detector module is used in a CT device, this is, for example, the direction along the axis of rotation (also referred to as the z-axis).

The retaining elements may be configured such that the retaining elements possess an increased mechanical stability in the form of a greater wall thickness owing to the use of a corresponding material or as a result of their geometric design. The retaining elements may be provided, for example, outside of the planar dimension of the sensor unit (e.g., of a converter unit of the sensor unit) in order to avoid the detection of X-rays being compromised. The retaining elements may be present integrally formed with the collimator module in a unitary construction or simply joined thereto, by adhesive bonding, for example. An epoxy glue may be used, for example.

With an adhesive bonding approach, a separate production of the retaining elements and of the collimator module may be provided, with the result, for example, that a more cost-effective method or a less expensive material may be used for the retaining elements than for the collimator module.

Providing a unitary solution enables the anti-scatter grid to be produced in just one manufacturing process, reduces the complexity of the structure, and may provide increased collimator stability.

For example, the anti-scatter grid may be produced by a technique known as rapid manufacturing, also referred to as additive manufacturing technology. Suitable candidates for this include, for example, selective laser melting using radiation-absorbing metallic powder (e.g., tungsten, molybdenum or tantalum).

The retaining elements may, for example, assume a shape that is advantageous for securely mounting the module on the carrier unit and that is coordinated with the carrier unit. For example, the retaining elements may be elongated in one direction or feature a projection relative to the collimator module. The shape of the retaining elements may be matched, for example, to the design of the carrier unit.

Further, the fastening means may be embodied on a side of the anti-scatter grid disposed opposite the sensor unit or on a lateral surface of the anti-scatter grid, the planar dimension of which surface extends parallel to the stacking direction of the stacking arrangement. In contrast to an embodiment on a side of the anti-scatter grid facing toward the sensor unit, for example, the fastening means may be more easily accessible for assembly purposes. A likelihood of damaging the sensor unit during assembly may be reduced.

According to a variant of the detector module, the anti-scatter grid also includes an adjustment means (e.g., an adjustment device) for positioning the anti-scatter grid relative to the carrier unit prior to the anti-scatter grid being fixed in place via the fastening means at least along one direction (e.g., along a direction of rotation or perpendicularly to a direction of rotation of a CT device). The adjustment means may also facilitate a relative positioning along more than one direction. The adjustment means may, for example, cooperatively interact with a corresponding (counter-)adjustment means embodied on the carrier unit. A positioning relative to the carrier unit may be simplified such that a secure mounting via the fastening means is easily made possible and in an aligned position. For example, an adjustment means may be configured as a guide pin or recess. An adjustment relative to the carrier unit would then be possible, for example, using an adjustment means in the form of the guide pin, whereas at the same time, the position of the anti-scatter grid may then be fixed via a screw-type connection using the fastening means in the aligned state. An adjustment means may also be configured, for example, as a stop surface that is provided on the anti-scatter grid and cooperatively interacts with the embodiment of the carrier unit. Other forms of adjustment means may also be provided.

According to an embodiment variant, the anti-scatter grid has at least one stop element for the sensor unit for the purpose of positioning the sensor unit relative to the anti-scatter grid. The sensor unit is then present in the stacking arrangement engaged fully home with the stop element.

An adjustment of the sensor unit relative to the anti-scatter grid may be implemented in a simplified manner. For example, a stop element may be configured in the form of a projection protruding over a radiation exit surface of the collimator module facing toward the sensor unit. The projection forms a stop surface for the sensor unit. The at least one stop element may be embodied, for example, on a collimator wall of the anti-scatter grid in the form of a projection along the stacking direction projecting beyond the wall height of the collimator wall. The stop element is arranged on the anti-scatter grid, for example, such that an area in the stacking arrangement facing toward the sensor unit on the radiation exit side of the anti-scatter grid, which is provided when a stacking arrangement is provided for arranging the sensor element, is limited by the stop element at least on one side by the stop surface of the stop element. For example, a plurality of stop elements that are arranged distributed on the anti-scatter grid such that on at least two sides the plurality of stop elements delimit an area that is equal to the planar dimension of a sensor element that is to be additionally disposed in a stacking arrangement in order to permit an improved alignment along two directions may be provided.

The stop element may be made of the same material as a collimator wall of the anti-scatter grid. The stop element may be present integrally formed in a unitary construction with the collimator wall on which the stop element may be arranged. The stop element may then be fabricated in a joint manufacturing step with the collimator wall on which the stop element is arranged. This may be implemented advantageously by a technique known as rapid manufacturing since, in this case, a high degree of variability in the embodiment of the collimator walls is made possible particularly easily.

According to an embodiment variant, the at least one stop element may also be present as detachable from the anti-scatter grid. For example, the stop element is connected to the anti-scatter grid via a predetermined breaking point in the form of a section having increased porosity or a narrower wall thickness. By a separation of the stop element following a relative positioning, it may be avoided that the stop element obstructs further construction steps.

The present embodiments further relate to an anti-scatter grid having fastening means for use in a detector module according to one of the previously described variants.

The anti-scatter grid may be provided, for example, according to one of the variants of the anti-scatter grid described in connection with the detector module. For example, the anti-scatter grid may be present with retaining elements and/or stop elements. An anti-scatter grid that reduces positioning tolerances occurring when providing a detector module and when installing the detector module in the X-ray detector may be provided.

The present embodiments further relate to an X-ray detector including at least one detector module and a carrier unit for the at least one detector module.

All embodiment variants described in the foregoing with reference to the detector module according to the present embodiments may also be implemented analogously in the X-ray detector. The description provided with regard to the detector module and the previously described advantages may also be applied analogously to the X-ray detector according to the present embodiments.

For example, the X-ray detector may include a plurality of detector modules arranged adjacent to one another, thereby achieving a greater detection area provided by the totality of detector modules.

For example, the carrier unit of the X-ray detector may include (counter-)fastening means (e.g., counter-fasteners) that are embodied in a corresponding manner to the fastening means (e.g., fasteners) of the detector module and cooperatively interact with these for the purpose of securely mounting the detector module. For example, the carrier unit of the X-ray detector may include a (counter-)adjustment means that is configured in a corresponding manner to potential adjustment means (e.g., adjustment device) of the detector module and cooperatively interacts with these for the purpose of positioning the detector module on the carrier unit. For example, the carrier unit may be part of a housing of the X-ray detector.

The present embodiments further relate to a computed tomography device including an X-ray detector according to one of the previously described variants and an X-ray source disposed opposite thereto, which is configured to expose the X-ray detector using X-rays.

For object scanning purposes, an object that is to be imaged may then be placed, for example, between the X-ray source and the detector module or the X-ray detector and irradiated by the X-ray source.

All embodiment variants described hereinabove with reference to the detector module according to the present embodiments and the X-ray detector according to the present embodiments may also be implemented analogously in the computed tomography device. The description provided with regard to the detector module and the X-ray detector and the previously described advantages may also be applied analogously to the computed tomography device according to the present embodiments.

Further, features described in relation to different embodiment variants of the invention may be combined within the scope of the invention to create further embodiment variants of the invention. In addition to the embodiment variants of the invention explicitly described in this application, many other embodiment variants of the invention that the person skilled in the art may realize without leaving the scope of the invention as set forth by means of the claims may be provided.

The use of the indefinite articles "a" or "an" does not exclude the possibility that the feature in question may also be present more than once. The use of the expression "comprise" does not rule out the possibility that the terms linked by the expression "comprise" may be identical. For example, the CT device comprises the CT device. The use of the term "unit" does not rule out the possibility that the object to which the term "unit" refers may include a plurality of components that are separated from one another in space.

BRIEF DESCRIPTION OF THE DRAWINGS

The invention is explained below with the aid of exemplary embodiment variants and with reference to the attached figures. The illustrations in the figures are schematic, greatly simplified, and not necessarily to scale. In the figures.

DETAILED DESCRIPTION

Figure 1:
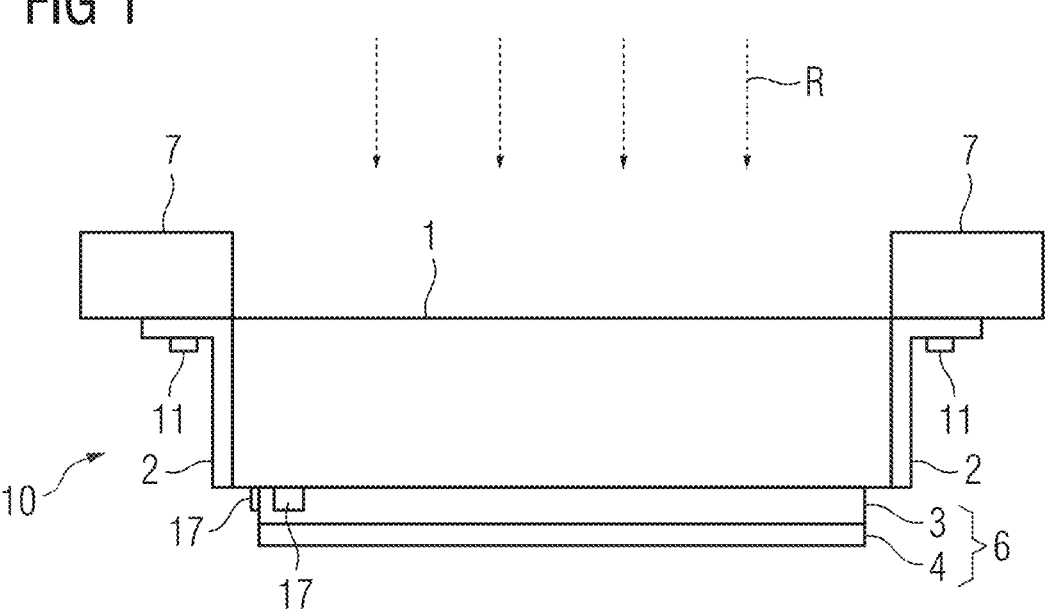
FIG. 1 shows a schematic view of a detector module mounted on a carrier unit of an X-ray detector.
Figure 2:
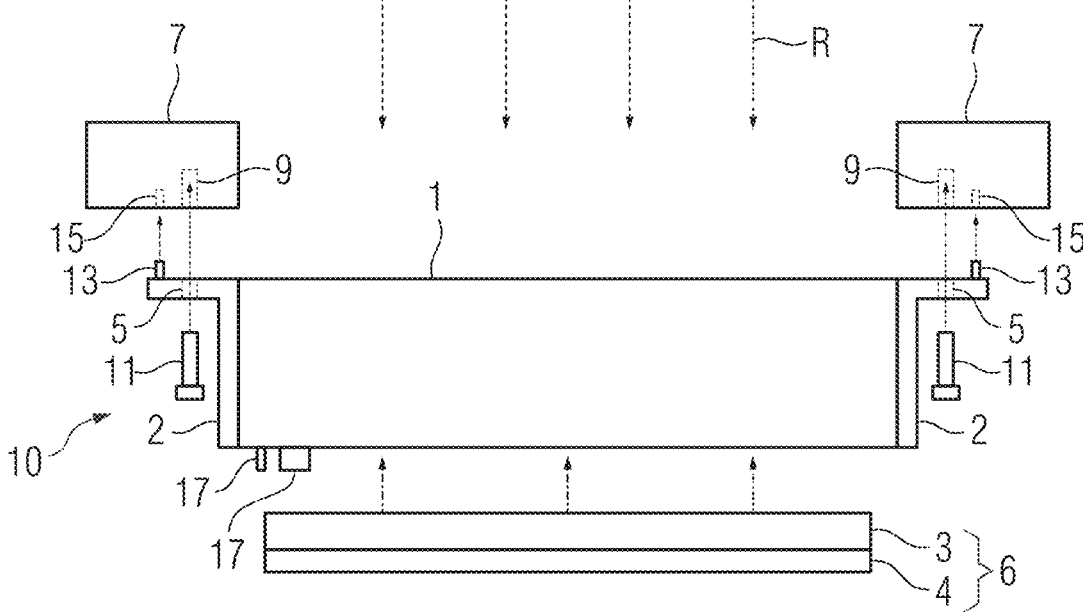
FIG. 2 shows a schematic view of the detector module from FIG. 1 in an at least partially disassembled illustration.

FIG. 1 shows a detector module in a state mounted on a carrier unit 7. FIG. 2 shows the same detector module as in FIG. 1 in an at least partially disassembled view in order to better illustrate the components and the manner of mounting. The following description therefore relates to both FIG. 1 and FIG. 2.

The detector module for an X-ray detector 36 includes a sensor unit 6 for detecting X-rays and an anti-scatter grid 10 in a stacking arrangement with the sensor unit 6. The sensor unit 6 is fixed in place on the anti-scatter grid 10.

The sensor unit 6 includes a converter unit 3 that is configured for converting incident X-rays into an electrical signal, and a readout unit 4 that is associated with the converter unit 3 and is configured for processing the electrical signals from the converter unit 3. The converter unit 3 is configured, for example, as a scintillator unit with a downstream photodiode array connected thereto. The readout unit 4 is configured as an ASIC, for example. In other variants, the converter unit 3 may also be configured as a direct-converting converter unit.

The anti-scatter grid 10 has fastening means 5 (e.g., fasteners) for securely mounting the detector module to the carrier unit 7 of the X-ray detector 36. The fastening means 5 may, for example, be configured as drilled holes that are provided for implementing a screw-type connection using a bolt 11 and, for this purpose, cooperatively interact with fastening means 9 (e.g., counter-fastening means; counter-fasteners) on the carrier unit 7, which may, for example, likewise be configured as drilled holes. The screw-type connection to the carrier unit 7 is then implemented parallel to the impinging X-rays R. The fastening means 5 are in this case configured on a side of the anti-scatter grid 10 disposed opposite the sensor unit 6.

In the example shown, the anti-scatter grid 10 includes a grid-shaped collimator module 1 composed of a plurality of collimator walls and having, on each of two opposite external sides of the collimator module 1, a retaining element 2 on which the fastening means 5 are embodied. In one embodiment, the collimator module may correspond to a three-dimensional (3D) collimator module including an arrangement of collimator walls extending along two directions perpendicular to the incident radiation incidence direction of the X-rays R. In this case, the retaining elements 2 are L-shaped, with a leg protruding laterally from the collimator module 1 in order to allow a screw-type connection parallel to the incident X-rays. In other embodiments, the retaining elements 2 may also be configured in some other way. In the example shown, the retaining elements 2 are indicated in addition as separate elements joined to the collimator module 1. For example, these are adhesively bonded to the collimator module 1. In alternative embodiments, the anti-scatter grid 10 is embodied integrally formed in a single piece.

Further, the anti-scatter grid 10 also includes adjustment means 13 (e.g., an adjustment device) for positioning the anti-scatter grid 10 relative to the carrier unit 7. The adjustment means cooperatively interact with adjustment means 15 (e.g., counter-adjustment means; a counter adjustment device) on the carrier unit 7. The adjustment means 13 and the counter-adjustment means 15 are, for example, configured as guide pins and mirror-inverted recesses, respectively. The adjustment means 13 and the counter-adjustment means 15 enable a relative positioning of the anti-scatter grid 10 on the carrier unit 7. This may also be implemented in other ways in other embodiments.

Additionally embodied on the anti-scatter grid 10 are stop elements 17 for the sensor unit 6 to allow positioning of the sensor unit 6 relative to the anti-scatter grid 10. The sensor unit 6 is then present in the stacking arrangement engaged fully home against the stop elements 17.

A respective stop element 17 is configured in the form of a projection protruding across a radiation exit surface of the collimator module 1 facing toward the sensor unit 6. The projection constitutes a stop surface for the sensor unit 6. In this case, the anti-scatter grid 10 shown includes two stop elements 17 that delimit an area that is provided for the arrangement of the sensor unit 6 on at least two sides in order to permit an improved alignment along two directions.

In embodiment variants, at least one stop element 17 may also be present as detachable from the anti-scatter grid 10. For example, the at least one stop element 17 is connected to the anti-scatter grid 10 via a predetermined breaking point such that by a separation of the at least one stop element 17 following a positioning of the sensor unit 6 relative to the anti-scatter grid 10, it may be avoided that the at least one stop element 17 impedes further construction steps.

Following the positioning of the sensor unit 6 relative to the anti-scatter grid 10, it is provided according to the present embodiments that the sensor unit 6 is fixed in place on the anti-scatter grid 10. This may be provided by a permanent adhesive bonding of the sensor unit 6 to the anti-scatter grid 10.

Figure 3:
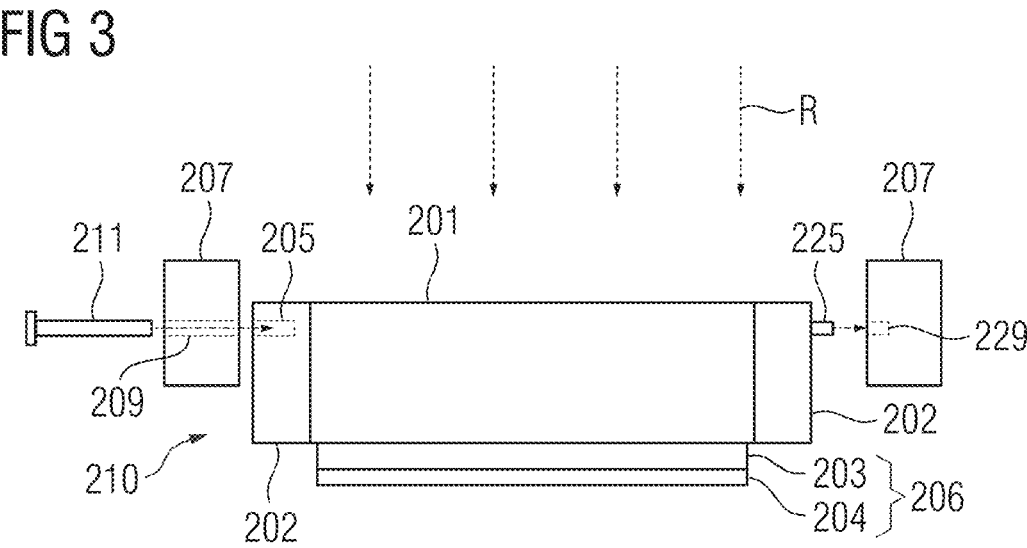
FIG. 3 and FIG. 4 show schematic views of detector modules according to further embodiments for mounting on a carrier unit of an X-ray detector.

FIG. 3 shows a detector module according to a further embodiment variant for mounting on a carrier unit 207 of an X-ray detector 36. According to the illustration in FIGS. 1 and 2, the detector module includes a sensor unit 206 for detecting X-rays R and an anti-scatter grid 210 in a stacking arrangement with the sensor unit 206. The sensor unit 206, including a converter unit 203 and a readout unit 204, is fixed in place on the anti-scatter grid 210 (e.g., adhesively bonded thereto). The anti-scatter grid 210 also has fastening means 205, 255 (e.g., fasteners) for securing the detector module to the carrier unit 207 of the X-ray detector 36.

The fastening means 205, 255 are embodied on retaining elements 202 of the anti-scatter grid 210. As in FIGS. 1 and 2, the retaining elements 202 are again indicated as separate elements joined to the collimator module 201. However, an integrally formed embodiment may also be employed.

In contrast to FIGS. 1 and 2, the fastening means 205, 225 are embodied on a side surface of the anti-scatter grid 210, the planar dimension of which extends parallel to the stacking direction of the stacking arrangement. This enables a lateral mounting of the detector module in a carrier unit 207 to be implemented. The fastening means 205, 225 are embodied differently. The fastening means 205 is, for example, configured as a drilled hole on one side of the anti-scatter grid 210 only. The fastening means 205 is provided with a drilled hole 209 in the carrier unit 207 as a counter-fastening means (e.g., counter-fastener) for a screw-type connection using a bolt 211. On the other, opposite side, the fastening means 225 is configured as a pin that may be inserted into a recess 229 embodied on the carrier unit 207 as a counter-fastening means (e.g., a counter-fastener) in order to realize a secure mounting on the carrier unit 207. However, there may also be other embodiments. As in FIGS. 1 and 2, adjustment means (e.g., an adjustment device) may be provided in this variant also in order to allow the anti-scatter grid 210 to be positioned relative to the carrier unit 207, and/or stop means (e.g., stops) may be provided for the sensor unit 206 in order to allow the sensor unit 206 to be positioned relative to the anti-scatter grid 210.

Figure 4:
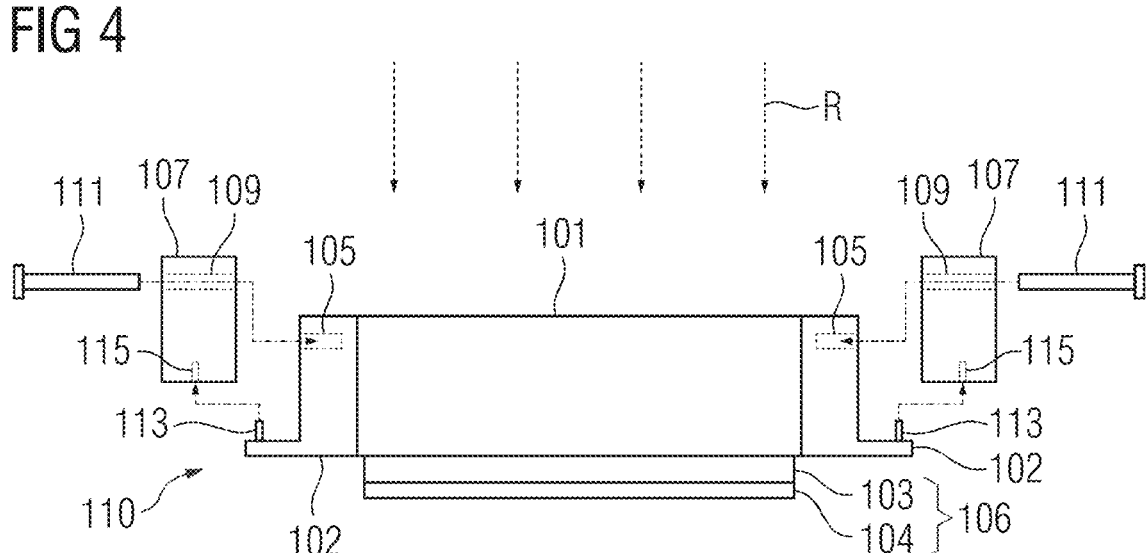

FIG. 4 shows a further variant of a detector module for mounting on a carrier unit 107 of an X-ray detector 36.

Similarly to the previously described variants, the detector module includes a sensor unit 106 for detecting X-rays R and an anti-scatter grid 110 in a stacking arrangement with the sensor unit 106. The sensor unit 106, including a converter unit 103 and a readout unit 104, is fixed in place on the anti-scatter grid 11 (e.g., adhesively bonded thereto). The anti-scatter grid 110 also has fastening means 105 (e.g., fasteners) for securely mounting the detector module on the carrier unit 107 of the X-ray detector 36.

The fastening means 105 are embodied on retaining elements 102 of the anti-scatter grid 110. As previously, the retaining elements 102 are again indicated as separate elements joined to the collimator module 101. However, a unitary embodiment in the form of a single piece may also be employed.

As in FIG. 3, the fastening means 105 are embodied on a lateral surface of the anti-scatter grid 110, the planar dimension of which extends parallel to the stacking direction of the stacking arrangement. In other words, a lateral mounting is provided. In contrast to FIG. 3, however, drilled holes 105 are provided on both sides as fastening means (e.g., fasteners) for a screw-type connection using a bolt 111. The fastening means cooperatively interact with corresponding counter-fastening means (e.g., counter-fasteners) configured as drilled holes 109 on the carrier unit 107. A screw-type connection on both sides may possibly lead to a higher mechanical stability of the structure.

The detector module also includes adjustment means 113 (e.g., an adjustment device) that are configured as guide pins, and cooperatively interact with counter-adjustment means (e.g., a counter-adjustment device) 115 on the carrier unit 107. The adjustment means 113 permit a precise insertion of the detector module in the carrier unit 107 prior to being screw-type in place and secured. Any adjustment means may also be configured in some other fashion. As in FIGS. 1 and 2, this variant may also be combined without difficulty with a stop element for the sensor unit 106 to allow positioning of the sensor unit 106 relative to the anti-scatter grid 110.

Figure 5:
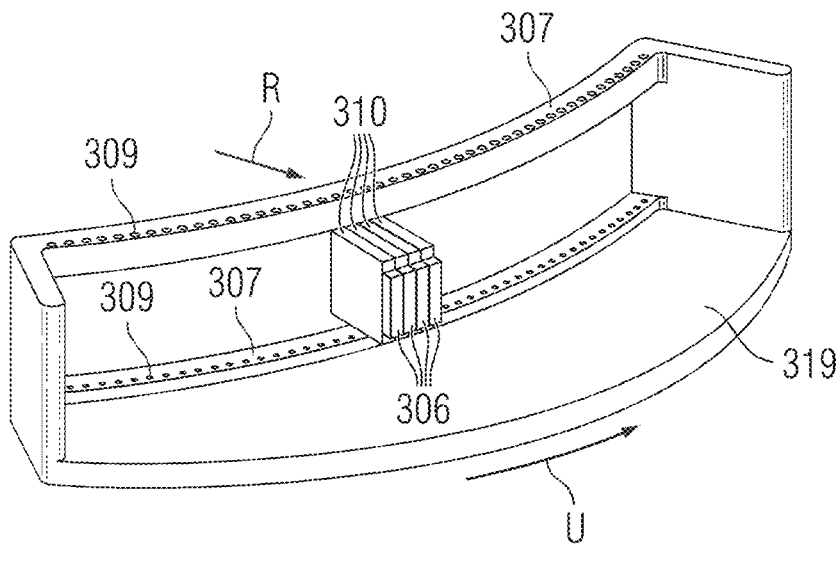
FIG. 5 shows a schematic view of a carrier unit of an X-ray detector for arranging a plurality of detector modules.

FIG. 5 shows a schematic view of a carrier unit 307 of an X-ray detector 36 intended for arranging a plurality of detector modules including an anti-scatter grid 310 and a sensor unit 306 in a stacking arrangement.

The modules shown in FIG. 5 provide a lateral mounting with the carrier unit similar to those described in connection with FIG. 3. The carrier unit 307 has corresponding drilled holes 309 that cooperatively interact with corresponding fastening means (e.g., fasteners) embodied on the anti-scatter grid 310. The carrier unit 307 is embodied in this case as part of a housing 319 of the X-ray detector 36 and forms two rails arranged in an arc shape that constitute a carrier frame for the detector modules on which a plurality of the detector modules may be arranged next to one another in the circumferential direction U. In this case, the carrier unit 307 is provided, for example, for use in a CT device. The circumferential direction U corresponds to the direction of rotation.

A similar embodiment that is geared to detector modules, as shown in FIG. 1, 2, or 4, for example, may be derived without difficulty by the person skilled in the art by adapting the carrier unit 207 in an appropriate manner. For example, a screw-type connection parallel to the incident X-rays R may also be provided by correspondingly configured fastening means (e.g., fasteners) on the detector module and corresponding (counter-)fastening means (e.g., counter-fasteners) on the carrier unit 307.

Figure 6:
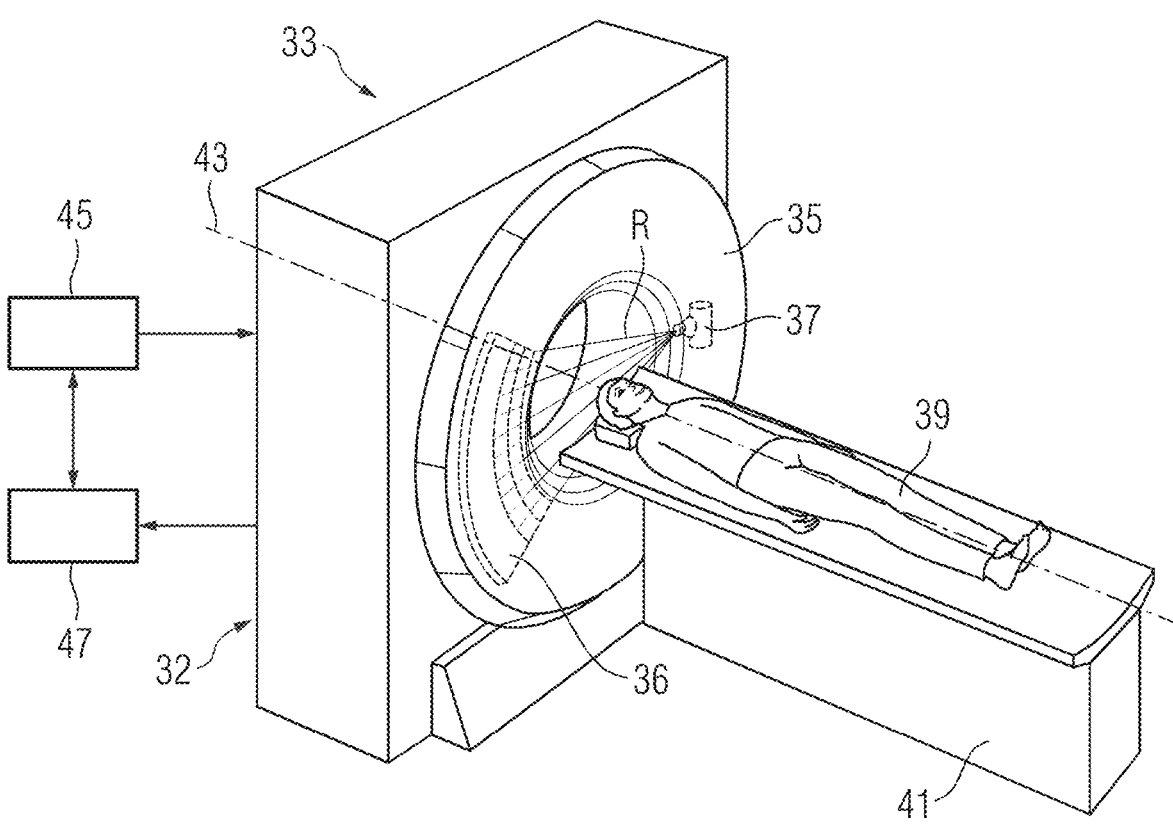
FIG. 6 shows a schematic view of a computed tomography device.

FIG. 6 also shows an example embodiment variant of a computed-tomography (CT) device 32 including an X-ray detector 36 and an X-ray source 37 disposed opposite the X-ray detector 36. The X-ray source 37 is configured to expose the X-ray detector 36 by X-rays along a radiation incidence direction. The CT device 32 includes a gantry 33 including a rotor 35. The rotor 35 includes the X-ray source 37 and the X-ray detector 36. The rotor 35 is rotatable around the axis of rotation 43. The examination object 39 (e.g., a patient) is positioned on the patient couch 41 and may be moved through the gantry 33 along the axis of rotation 43. A computing unit 45 is used to control the computed tomography device and to calculate slice images or volume-rendered images of the object. The computing unit 45 in the form of a computer system is configured to reconstruct X-ray image data based on the data of the X-ray detector 36 of the computed tomography device. A further computer system serves as an operator console 47. The software installed on the operator console 47 enables the operator to control the operation of the computed tomography system, such as, for example, the selection of a protocol, the starting of the scanning, etc. The operator console 47 may also be configured as a computer system.

The X-ray detector 36 may, for example, include a plurality of detector modules, as described hereinabove, that are arranged in an arc (e.g., similar or identical to that shown in FIG. 5) on a carrier unit 7, 107, 207, 307, such that an advantageously large total detection area of the X-ray detector 36 may be embodied overall by a sequential arrangement of the respective detection surfaces of the sensor units 6, 106, 206, 306.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A detector module for an X-ray detector, the detector module comprising:
   at least one sensor unit operable to detect X-rays; and
   at least one anti-scatter grid in a stacking arrangement with the at least one sensor unit,
      wherein the at least one sensor unit is fixed in place on the at least one anti-scatter grid, and wherein the at least one anti-scatter grid comprises a fastener operable to securely mount the at least one anti-scatter grid of the detector module onto a carrier unit of the X-ray detector such that the at least one anti-scatter grid is positioned between the at least one sensor unit and the carrier unit.

2. The detector module of claim 1, wherein the at least one anti-scatter grid further comprises a collimator module, and
   wherein the collimator module comprises a plurality of collimator walls and, on each external side of two opposite external sides of the collimator module, a retaining element on which the fastener is configured.

3. The detector module of claim 2, wherein the collimator module is produced in a single piece with the retaining elements.

4. The detector module of claim 1, wherein the fastener is configured as a drilled hole, a pin, or the drilled hole and the pin.

5. The detector module of claim 1, wherein the fastener is positioned on a side of the one anti-scatter grid opposite the at least one sensor unit, and
   wherein the fastener extends in a direction parallel to the X-rays configured to be detected by the at least one sensor unit.

6. The detector module of claim 1, wherein the at least one anti-scatter grid further comprises an adjustment device to allow positioning of the at least one anti-scatter grid relative to the carrier unit along at least one direction.

7. The detector module of claim 1, wherein the at least one sensor unit is adhesively bonded to the at least one anti-scatter grid.

8. The detector module of claim 1, wherein the at least one anti-scatter grid further comprises at least one stop element for the at least one sensor unit to allow positioning of the at least one sensor unit relative to the at least one anti-scatter grid, and
   wherein the at least one sensor unit is present in the stacking arrangement engaged fully home against the at least one stop element.

9. The detector module of claim 1, wherein the fastener is positioned on a lateral surface of the at least one anti-scatter grid, a planar dimension of which extends parallel to a stacking direction of the stacking arrangement.

10. A detector module comprising:
   at least one sensor unit operable to detect X-rays; and
   an anti-scatter grid in a stacking arrangement with the at least one sensor unit, wherein the at least one sensor unit is fixed in place on the anti-scatter grid,
   wherein the anti-scatter grid comprises a fastener operable to securely mount the detector module on a carrier unit of an X-ray detector such that the anti-scatter grid is positioned between the at least one sensor unit and the carrier unit.

11. An X-ray detector comprising:
   a carrier unit; and
   at least one detector module, wherein a detector module of the at least one detector module comprises:
      at least one sensor unit operable to detect X-rays; and
      at least one anti-scatter grid in a stacking arrangement with the at least one sensor unit, wherein the at least one sensor unit is fixed in place on the at least one anti-scatter grid, and wherein the at least one anti-scatter grid comprises a fastener operable to securely mount the at least one anti-scatter grid of the detector module onto the carrier unit of the X-ray detector such that the at least one anti-scatter grid is positioned between the at least one sensor unit and the carrier unit.

12. The X-ray detector of claim 11, wherein the at least one anti-scatter grid further comprises a collimator module, the collimator module comprising at least a plurality of collimator walls and, on each of two opposite external sides of the collimator module, a retaining element on which the fastener is configured.

13. The X-ray detector of claim 12, wherein the collimator module is produced in a single piece with the retaining elements.

14. The X-ray detector of claim 11, wherein the fastener is configured as a drilled hole, a pin, or the drilled hole and the pin.

15. The X-ray detector of claim 11, wherein the fastener is configured on a side of the at least one sensor unit opposite the at least one anti-scatter grid or on a lateral surface of the at least one anti-scatter grid, a planar dimension of which extends parallel to a stacking direction of the stacking arrangement.

16. The X-ray detector of claim 11, wherein the at least one anti-scatter grid further comprises an adjustment device to allow positioning of the at least one anti-scatter grid relative to the carrier unit along at least one direction.

17. The X-ray detector of claim 11, wherein the at least one sensor unit is adhesively bonded to the at least one anti-scatter grid.

18. The X-ray detector of claim 11, wherein the at least one anti-scatter grid further comprises at least one stop element for the at least one sensor unit to allow positioning of the at least one sensor unit relative to the at least one anti-scatter grid, and wherein the at least one sensor unit is present in the stacking arrangement engaged fully home against the at least one stop element.

19. A computed tomography device comprising:

an X-ray detector comprising:

a carrier unit; and at least one detector module, wherein a detector module of the at least one detector module comprises:

at least one sensor unit operable to detect X-rays; and at least one anti-scatter grid in a stacking arrangement with the at least one sensor unit, wherein the at least one sensor unit is fixed in place on the at least one anti-scatter grid, and wherein the at least one anti-scatter grid comprises a fastener operable to securely mount the at least one anti-scatter grid of the detector module onto the carrier unit of the X-ray detector such that the at least one anti-scatter grid is positioned between the at least one sensor unit and the carrier unit; and an X-ray source disposed opposite the X-ray detector.

* * * * *